United States Patent
Hamamoto et al.

(10) Patent No.: US 11,433,224 B2
(45) Date of Patent: Sep. 6, 2022

(54) METHOD FOR MANUFACTURING HOLLOW NEEDLING IMPLEMENT, DEVICE FOR MANUFACTURING HOLLOW NEEDLING IMPLEMENT, AND HOLLOW NEEDLING IMPLEMENT

(71) Applicant: KAO CORPORATION, Tokyo (JP)

(72) Inventors: Shinji Hamamoto, Shimotsuke (JP); Takatoshi Niitsu, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 317 days.

(21) Appl. No.: 16/646,722

(22) PCT Filed: Jun. 14, 2018

(86) PCT No.: PCT/JP2018/022719
§ 371 (c)(1),
(2) Date: Mar. 12, 2020

(87) PCT Pub. No.: WO2019/053977
PCT Pub. Date: Mar. 21, 2019

(65) Prior Publication Data
US 2020/0269029 A1    Aug. 27, 2020

(30) Foreign Application Priority Data
Sep. 13, 2017    (JP) .............................. JP2017-175950

(51) Int. Cl.
*A61M 37/00*    (2006.01)
*B29C 51/42*    (2006.01)

(52) U.S. Cl.
CPC ......... *A61M 37/0015* (2013.01); *B29C 51/42* (2013.01); *A61M 2037/003* (2013.01);
(Continued)

(58) Field of Classification Search
CPC ............. B29C 51/42; H05B 1/02; A61M 5/32
See application file for complete search history.

(56) References Cited

U.S. PATENT DOCUMENTS

| | | | |
|---|---|---|---|
| 2002/0020688 A1* | 2/2002 | Sherman | ................... B26F 1/24 216/2 |
| 2005/0178760 A1* | 8/2005 | Chang | ................. B29C 35/0888 219/497 |

(Continued)

FOREIGN PATENT DOCUMENTS

| | | |
|---|---|---|
| CN | 101297989 A | 11/2008 |
| DE | 100 65 188 A1 | 7/2002 |

(Continued)

OTHER PUBLICATIONS

International Search Report issued in PCT/JP2018/022719 (PCT/ISA/210), dated Sep. 11, 2018.
U.S. Appl. No. 15/519,440, filed Apr. 14, 2017.

*Primary Examiner* — Cachet I Proctor
(74) *Attorney, Agent, or Firm* — Birch, Stewart, Kolasch & Birch, LLP

(57) ABSTRACT

A method for manufacturing a hollow protruding implement (1) including a fine hollow protrusion (3) having an opening (3*h*) of the present invention includes a protrusion forming step of inserting a projecting mold part (11) into a base material sheet (2A) from one face (2D) side thereof, the base material sheet containing a thermoplastic resin, thereby forming a non-penetrated hollow protrusion (3) projecting from another face (2U) side of the base material sheet (2A). Subsequently, an opening forming step is performed in which an opening (3*h*) that penetrates the hollow protrusion (3) is formed by using a contactless opening forming means disposed on the other face (2U) side of the base material sheet (2A).

22 Claims, 6 Drawing Sheets

(52) U.S. Cl.
CPC ............... *A61M 2037/0023* (2013.01); *A61M 2037/0053* (2013.01); *A61M 2207/10* (2013.01)

(56) References Cited

U.S. PATENT DOCUMENTS

| | | | |
|---|---|---|---|
| 2006/0048521 A1* | 3/2006 | Katayama | F28F 3/044 165/4 |
| 2008/0097352 A1* | 4/2008 | Beck | A61B 5/14542 29/874 |
| 2008/0307849 A1* | 12/2008 | Lim | A61M 37/0015 204/242 |
| 2009/0093775 A1 | 4/2009 | Raju et al. | |
| 2009/0234301 A1* | 9/2009 | Tomono | A61M 37/0015 604/272 |
| 2012/0041337 A1 | 2/2012 | Ferguson et al. | |
| 2012/0172820 A1 | 7/2012 | Cannehan et al. | |
| 2016/0136406 A1* | 5/2016 | Berry | A61B 5/150984 604/173 |
| 2016/0354521 A1 | 12/2016 | Sumida | |
| 2017/0239855 A1* | 8/2017 | Niitsu | A61M 37/0015 |
| 2019/0030308 A1 | 1/2019 | Niitsu et al. | |

FOREIGN PATENT DOCUMENTS

| | | | | |
|---|---|---|---|---|
| JP | 7-308383 | A | | 11/1995 |
| JP | 2002-172169 | A | | 6/2002 |
| JP | 2002172169 | A | * | 6/2002 |
| JP | 2011-72695 | A | | 4/2011 |
| JP | 2012-523270 | A | | 10/2012 |
| JP | 2012-532709 | A | | 12/2012 |
| JP | 2017-35432 | A | | 2/2017 |
| JP | 2017-131397 | A | | 8/2017 |
| JP | 2017131397 | A | * | 8/2017 ............ A61M 37/00 |
| JP | 2017-176655 | A | | 10/2017 |
| WO | WO 2015/125475 | A1 | | 8/2015 |
| WO | WO 2017/170816 | A1 | | 10/2017 |

* cited by examiner

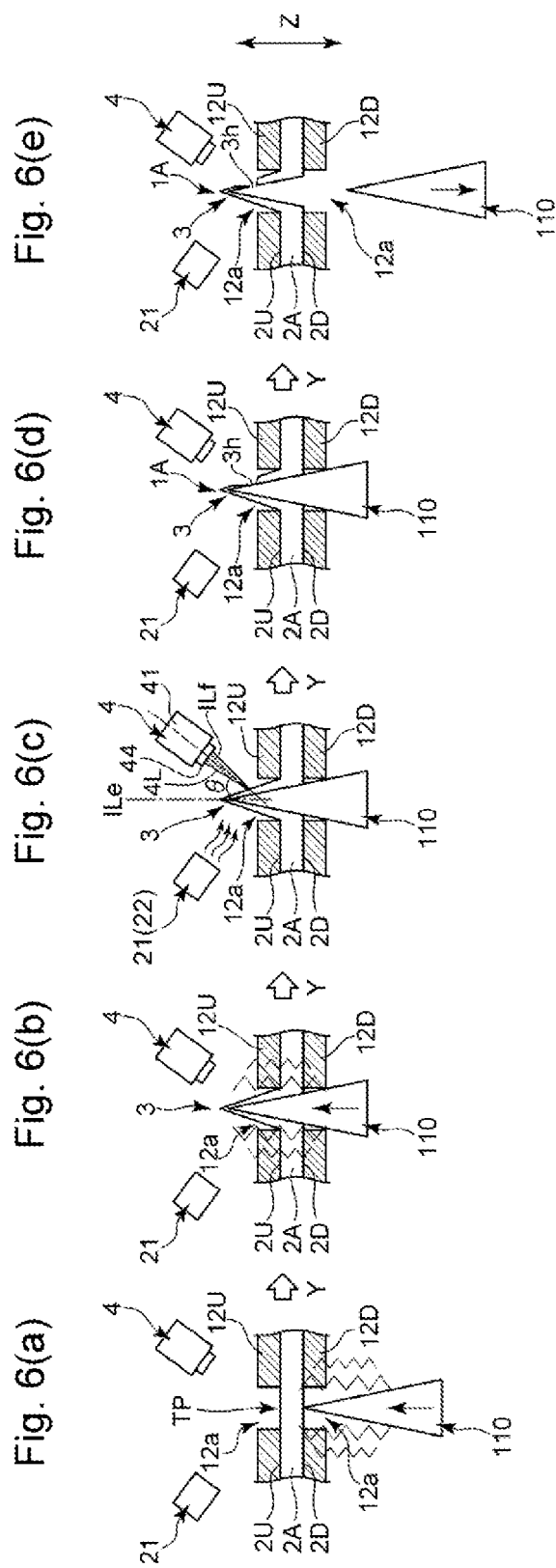

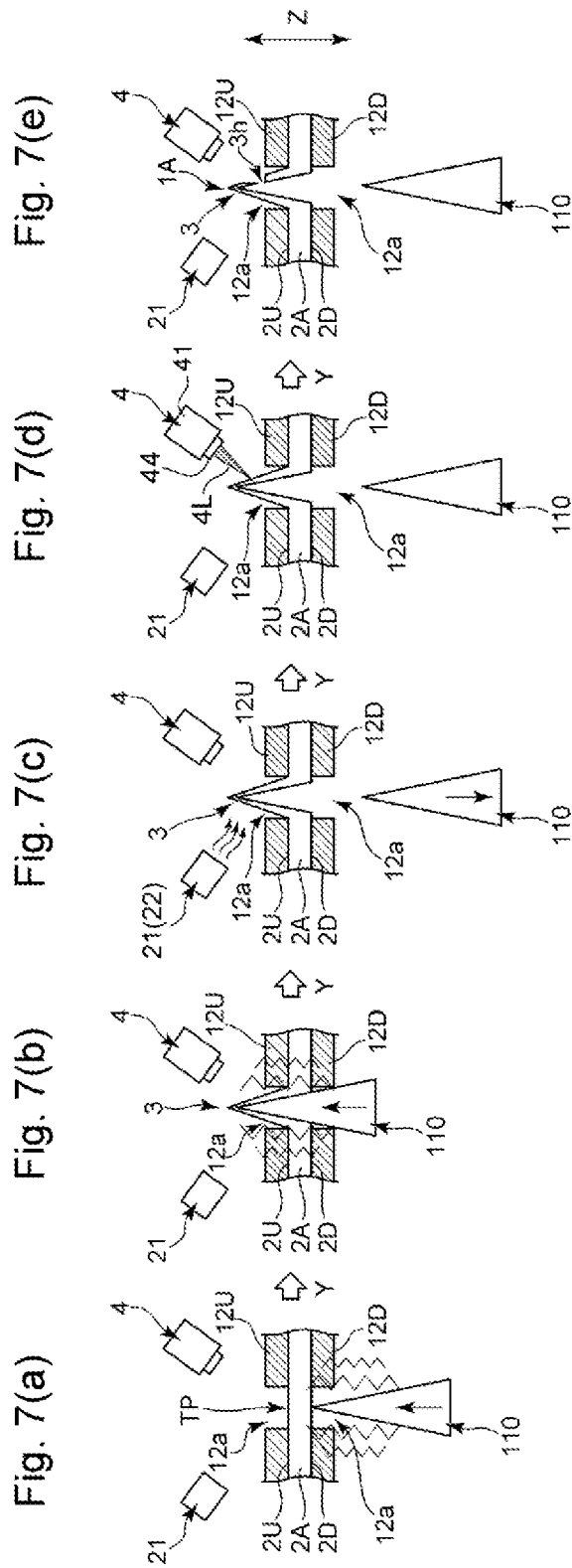

METHOD FOR MANUFACTURING HOLLOW NEEDLING IMPLEMENT, DEVICE FOR MANUFACTURING HOLLOW NEEDLING IMPLEMENT, AND HOLLOW NEEDLING IMPLEMENT

TECHNICAL FIELD

The present invention relates to a method and an apparatus for manufacturing a hollow protruding implement including a fine hollow protrusion having an opening. Also, the present invention relates to a hollow protruding implement including a fine hollow protrusion having an opening.

BACKGROUND ART

Recently, the delivery of agents using microneedles has been gaining attention in the fields of medicine and cosmetics. When using microneedles, which are fine needles, to pierce the skin to a shallow layer, the same performance as when delivering agents using syringes can be achieved without inducing pain. The applicant has proposed a method for manufacturing a fine hollow protruding article with a hollow interior (Patent Literature 1). Among microneedles, in particular, hollow microneedles with openings are effective because they can increase the number of choices of agents to be provided inside the microneedles. However, particularly when used in the fields of medicine or cosmetics, hollow microneedles with openings need to have a high level of precision in their shape, and to have a level of stability that enables stable delivery of agents through the openings into the skin.

Hollow microneedles with openings can be manufactured, for example, using manufacturing methods disclosed in Patent Literatures 2 to 4. Patent Literature 2 discloses a method for manufacturing a hollow microneedle array through injection molding using a mold part having a plurality of depressions formed in advance and a mold part having a plurality of projections formed in advance such that the projections are respectively inserted into the depressions.

Patent Literature 3 discloses a method for manufacturing fine microneedles with openings by forming openings in fine solid microneedles reproduced on a substrate through heat imprinting, the openings being formed by applying short pulse laser light from a back face side of the substrate, and penetrating the substrate and the microneedles.

Patent Literature 4 discloses a method for manufacturing a hollow needle-shaped body with a through hole, the method including producing a needle-shaped body having a solid protrusion projecting from one face of a substrate through injection molding or the like, and then forming a through hole in the needle-shaped body, the through-hole penetrating both the substrate and the protrusion, by applying laser light from another face side of the substrate.

CITATION LIST

Patent Literature

Patent Literature 1: US 2017/0239855A1
Patent Literature 2: US 2012/0041337A1
Patent Literature 3: JP 2011-72695A
Patent Literature 4: US 2016/0354521A1

SUMMARY OF INVENTION

The present invention is directed to a method for manufacturing a hollow protruding implement including a fine hollow protrusion having an opening. The present invention includes a protrusion forming step of inserting a protrusion-forming projecting mold part into a base material sheet from one face side thereof, the base material sheet containing a thermoplastic resin, thereby forming a non-penetrated hollow protrusion projecting from another face side of the base material sheet. The present invention provides a method for manufacturing a hollow protruding implement, the method including an opening forming step of forming an opening that penetrates the non-penetrated hollow protrusion by using a contactless opening forming means that is disposed on the other face side of the base material sheet.

Also, the present invention is directed to a hollow protruding implement including a fine hollow protrusion having an opening. The opening is a through hole disposed at a position offset from the center of a tip portion of the hollow protrusion. The present invention provides a hollow protruding implement in which the inner diameter of the opening on an outer surface side of the hollow protrusion is greater than the inner diameter thereof on an inner surface side of the hollow protrusion.

Also, the present invention is directed to an apparatus for manufacturing a hollow protruding implement including a fine hollow protrusion having an opening. The present invention has a protrusion forming section including a protrusion-forming projecting mold part that is disposed on one face side of a base material sheet containing a thermoplastic resin, and an opening forming section including a contactless opening forming means that is disposed on the other face side of the base material sheet. The present invention provides an apparatus for manufacturing a hollow protruding implement, the apparatus being configured to insert the projecting mold part into the base material sheet from the one face side thereof, thereby forming a non-penetrated hollow protrusion projecting from the other face side of the base material sheet, and to subsequently form an opening as a through hole in the non-penetrated hollow protrusion by using the opening forming means from the other face side of the base material sheet.

BRIEF DESCRIPTION OF DRAWINGS

FIGS. 6(a) to 6(e) illustrate a method for manufacturing a hollow protruding implement including a fine hollow protrusion having an opening, with the use of the manufacturing apparatus shown in FIG. 4.

FIGS. 7(a) to 7(e) illustrate a manufacturing method for manufacturing the hollow protruding implement shown in FIG. 1 according to another embodiment.

DESCRIPTION OF EMBODIMENTS

According to the manufacturing method disclosed in Patent Literature 2, manufacture is performed using injection molding, and thus the temperature is likely to vary between a depressed mold part and a projecting mold part that are used, and the mold parts are likely to be deformed by being worn down. Thus, it is difficult to manufacture microneedles with a precise shape, which makes it difficult to stably deliver agents through the openings into the skin. Moreover, according to the manufacturing method disclosed in Patent Literature 2, after hollow microneedles have been formed, the hollow microneedles are laser drilled through the interiors thereof to form openings. Thus, burrs are likely to be formed around the openings on outer surfaces of the microneedles, which may in turn make it difficult to pierce the skin.

According to the manufacturing methods disclosed in Patent Literatures 3 and 4, after solid microneedles have been formed on a substrate in a separate step, openings are formed by applying laser light from a back face side of the substrate as postprocessing, and therefore, as is the case with the manufacturing method disclosed in Patent Literature 2, burrs are likely to be formed around the openings on the outer surfaces of the microneedles. Moreover, according to the manufacturing methods disclosed in Patent Literatures 3 and 4, since the openings that penetrate the substrate and the solid microneedles are formed by applying laser light from the back face side of the substrate, the laser light is required to have high irradiation energy, which makes it difficult to manufacture fine microneedles with a precise shape.

Therefore, the present invention relates to a method and an apparatus for manufacturing a fine hollow protruding implement having an opening, with which a fine hollow protrusion can be formed with a precise shape, and burrs are unlikely to be formed around the opening on the outer surface of the hollow protrusion. Moreover, the present invention relates to a fine hollow protruding implement having an opening, the implement being capable of easily piercing the skin.

Hereinafter, the present invention will be described with reference to the drawings based on preferred embodiments.

Figure 1:
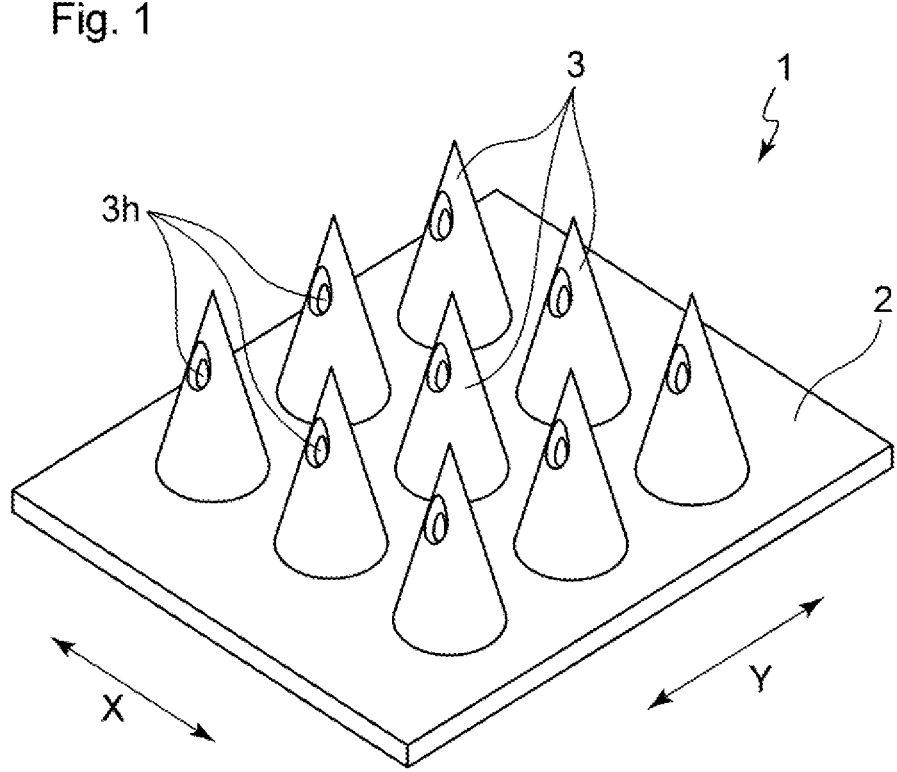
FIG. 1 is a schematic perspective view of an example of a hollow protruding implement in which fine hollow protrusions having openings are arranged in an array, manufactured using a method for manufacturing a hollow protruding implement of the present invention.

FIG. 1 shows a perspective view of a hollow protruding implement 1 according to a preferred embodiment of a hollow protruding implement of the present invention. The hollow protruding implement 1 includes fine hollow protrusions 3 that have openings 3h on a tip side thereof, and a flat basal member 2. The hollow protruding implement 1 has a form in which a plurality of hollow protrusions 3 project from the basal member 2.

There is no particular limitation on the number of hollow protrusions 3, the arrangement of the hollow protrusions 3, and the shape of the hollow protrusions 3, but, in the hollow protruding implement 1 shown in FIG. 1, nine conical hollow protrusions 3 are arranged in an array on the upper face of the sheet-like basal member 2. The nine hollow protrusions 3 arranged in an array are arranged in three rows along a first direction (direction Y), which is the direction in which a base material sheet 2A, which will be described later, is transported (the longitudinal direction of the base material sheet 2A), and in three columns along a second direction (direction X), which is the direction orthogonal to the transporting direction and which is the lateral direction of the base material sheet 2A that is being transported. Note that FIG. 2 is a perspective view of the hollow protruding implement 1 focusing on one hollow protrusion 3 from among the hollow protrusions 3 arranged in an array included in the hollow protruding implement 1, and FIG. 3 is a cross-sectional view taken along line III-III shown in FIG. 2.

Figure 2:
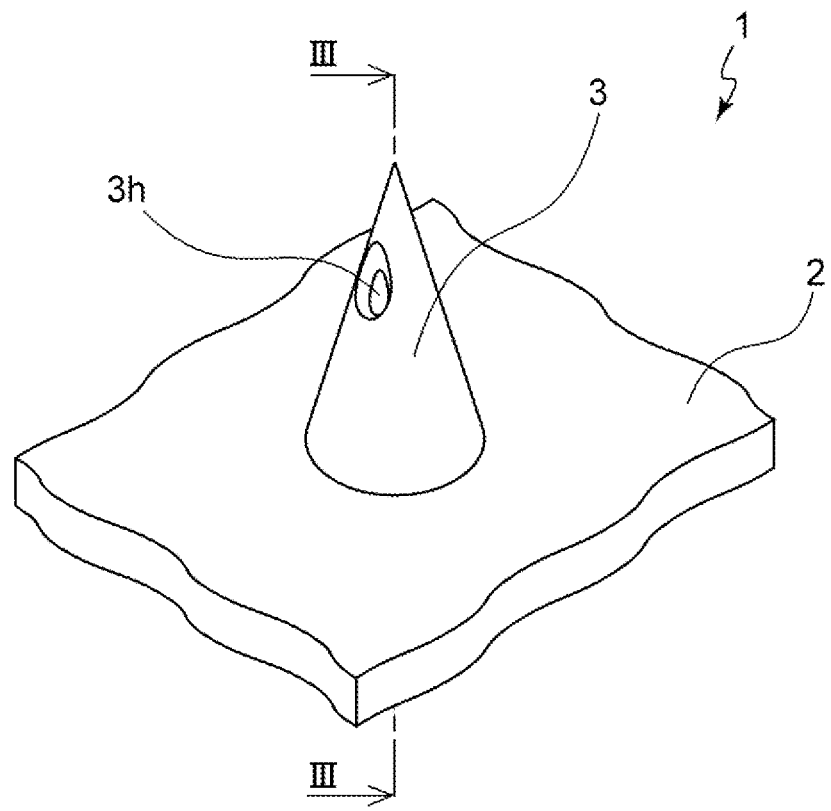
FIG. 2 is a perspective view of the hollow protruding implement focusing on one hollow protrusion, of the plurality of hollow protrusions shown in FIG. 1.
Figure 3:
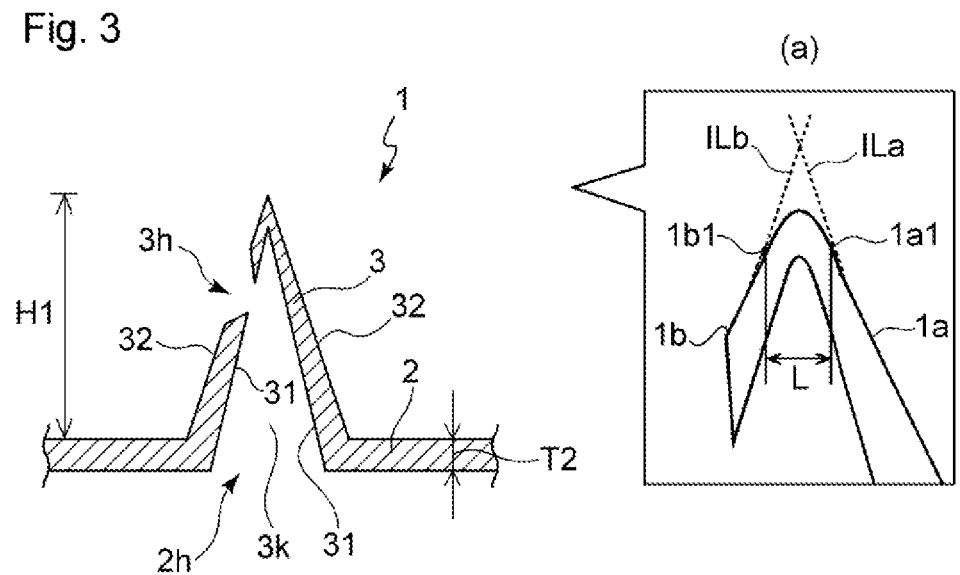
FIG. 3 is a cross-sectional view taken along line III-III shown in FIG. 2.

As shown in FIG. 2, the hollow protruding implement 1 has the openings 3h, which are through holes, in the respective hollow protrusions 3. As shown in FIG. 3, the hollow protruding implement 1 has basal-side openings 2h in the basal member 2 at positions corresponding to the respective hollow protrusions 3. As shown in FIG. 3, spaces 3k are formed in the hollow protruding implement 1 and individually extend from the basal-side openings 2h in the basal member 2 to the openings 3h on the tip side through the interiors of the hollow protrusions 3. Therefore, the openings 3h are in communication with the spaces 3k in the respective hollow protrusions 3. The spaces 3k in the hollow protrusions 3 are formed in a shape that conforms to the outer shape of the hollow protrusions 3, and, in the hollow protruding implement 1 shown in FIG. 1, they are formed in a conical shape, which is a shape that conforms to the outer shape of the conical hollow protrusions 3. Note that, although the hollow protrusions 3 have a conical outer shape, they may have a truncated conical shape, a cylindrical shape, a prism shape, a pyramidal shape, a truncated pyramidal shape, or the like instead of a conical shape.

As shown in FIG. 2, each opening 3h is a through hole that is formed at a position offset from the center of the tip portion of a corresponding one of the hollow protrusions 3. If the openings 3h are formed at positions offset from the centers of the tip portions of the hollow protrusions 3 in this manner, when using the hollow protrusions 3 of the hollow protruding implement 1 to pierce the skin, the openings 3h are unlikely to be crushed, and thus it is possible to stably deliver agents from the hollow protruding implement 1 through the openings 3h into the skin.

Each hollow protrusion 3, when used as a microneedle, is inserted such that the tip of the hollow protrusion 3 reaches the stratum corneum, which is the outermost layer, or the dermis, which is a deeper layer, and thus a projecting height H1 (see FIG. 3) thereof is preferably 0.01 mm or greater, and more preferably 0.02 mm or greater, is preferably 10 mm or less, and more preferably 5 mm or less, and, specifically, is preferably from 0.01 to 10 mm, and more preferably from 0.02 to 5 mm.

A tip diameter L (see FIG. 3(a)) of each hollow protrusion 3, that is, the distance between outer surface portions 32 of that hollow protrusion 3 at the tip thereof, is preferably 1 μm or greater, and more preferably 5 μm or greater, is preferably 500 μm or less, and more preferably 300 μm or less, and, specifically, is preferably from 1 to 500 μm, and more preferably from 5 to 300 μm. The tip diameter L of the hollow protruding implement 1 is the length at a position where the length is longest at the tip of a hollow protrusion 3. If the tip diameter L is within the above-described range, there is almost no pain when the hollow protruding implement 1 is inserted into the skin. The tip diameter L is measured as follows.

Measurement of Tip Diameter of Hollow Protrusions 3 in Hollow Protruding Implement 1

The tip portion of a hollow protrusion 3 is magnified at a predetermined magnification as shown in FIG. 3(a) and observed using a scanning electron microscope (SEM) or a microscope.

Next, as shown in FIG. 3(a), an imaginary straight line ILa is extended along the straight-line portion of one lateral side 1a of two lateral sides 1a and 1b defining the outer surface 32, and an imaginary straight line ILb is extended along the straight-line portion of the other lateral side 1b. Next, the point where the lateral side 1a separates from the imaginary straight line ILa on the tip side is obtained as a first tip point 1a1, and the point where the other lateral side 1b separates from the imaginary straight line ILb is obtained as a second tip point 1b1. A length L of a straight line that links the thus obtained first tip point 1a1 and second tip point 1b1 is measured using a scanning electron microscope (SEM) or a microscope, and the measured length of the straight line is taken as the tip diameter of the hollow protrusion 3.

An opening area S1 of each opening 3h at an inner surface 31 of the hollow protrusion 3 is preferably 0.7 $\mu m^2$ or greater, and more preferably 20 $\mu m^2$ or greater, is preferably 200,000 $\mu m^2$ or less, and more preferably 70,000 $\mu m^2$ or less, and, specifically, is preferably from 0.7 to 200,000 $\mu m^2$, and more preferably from 20 to 70,000 $\mu m^2$.

As shown in FIG. 3, the opening 3h is formed such that the opening area thereof on the outer surface 32 side of the hollow protrusion 3 is larger than the opening area S1 thereof on the inner surface 31 side of the hollow protrusion 3. That is to say, the opening 3h is formed such that the inner diameter thereof on the outer surface 32 side of the hollow protrusion 3 is greater than the inner diameter thereof on the inner surface 31 side of the hollow protrusion 3. The inner diameter on the inner surface 31 side is the diameter at the widest point of the opening 3h that is formed at the inner surface 31, and the inner diameter on the outer surface 32 side is the diameter at the widest point of the opening 3h that is formed at the outer surface 32. From the viewpoint of stably delivering agents into the skin through the openings 3h of the hollow protrusions 3, the inner diameter of the openings 3h on the inner surface 31 side is preferably 1 $\mu m$ or greater, and more preferably 5 $\mu m$ or greater, is preferably 500 $\mu m$ or less, and more preferably 300 $\mu m$ or less, and, specifically, is preferably from 1 to 500 $\mu m$, and more preferably from 5 to 300 $\mu m$. From the same viewpoint, the inner diameter of the opening 3h on the outer surface 32 side is preferably 1.1 or more times, and more preferably 1.2 or more times, is preferably 15 or less times, and more preferably 10 or less times, and, specifically, is preferably from 1.1 to 15 times, and more preferably from 1.2 to 10 times greater than the inner diameter on the inner surface 31 side. From the viewpoint of even more stably delivering agents into the skin through the openings 3h of the hollow protrusions 3, it is preferable that the inner diameter of each opening 3h gradually increases from the inner surface 31 side of the hollow protrusion 3 toward the outer surface 32 side thereof.

The opening area S2 of each basal-side opening 2h at a lower face of the basal member 2, which is opposite to the upper face thereof on which the hollow protrusions 3 are arranged, is preferably 0.007 $mm^2$ or greater, and more preferably 0.03 $mm^2$ or greater, is preferably 20 $mm^2$ or less, and more preferably 7 $mm^2$ or less, and, specifically, is preferably from 0.007 to 20 $mm^2$, and more preferably from 0.03 to 7 $mm^2$.

The nine hollow protrusions 3 arranged in an array on the upper face of the sheet-like basal member 2 are preferably such that the center-to-center distance in the first direction Y is uniform and the center-to-center distance in the second direction X is uniform, and, preferably, the center-to-center distance in the first direction Y is the same as the center-to-center distance in the second direction X. Preferably, the center-to-center distance in the first direction Y between the hollow protrusions 3 is preferably 0.01 mm or greater, and more preferably 0.05 mm or greater, is preferably 10 mm or less, and more preferably 5 mm or less, and, specifically, is preferably from 0.01 to 10 mm, and more preferably from 0.05 to 5 mm. Furthermore, the center-to-center distance in the second direction X between the hollow protrusions 3 is preferably 0.01 mm or greater, and more preferably 0.05 mm or greater, is preferably 10 mm or less, and more preferably 5 mm or less, and, specifically, is preferably from 0.01 to 10 mm, and more preferably from 0.05 to 5 mm.

Figure 4:
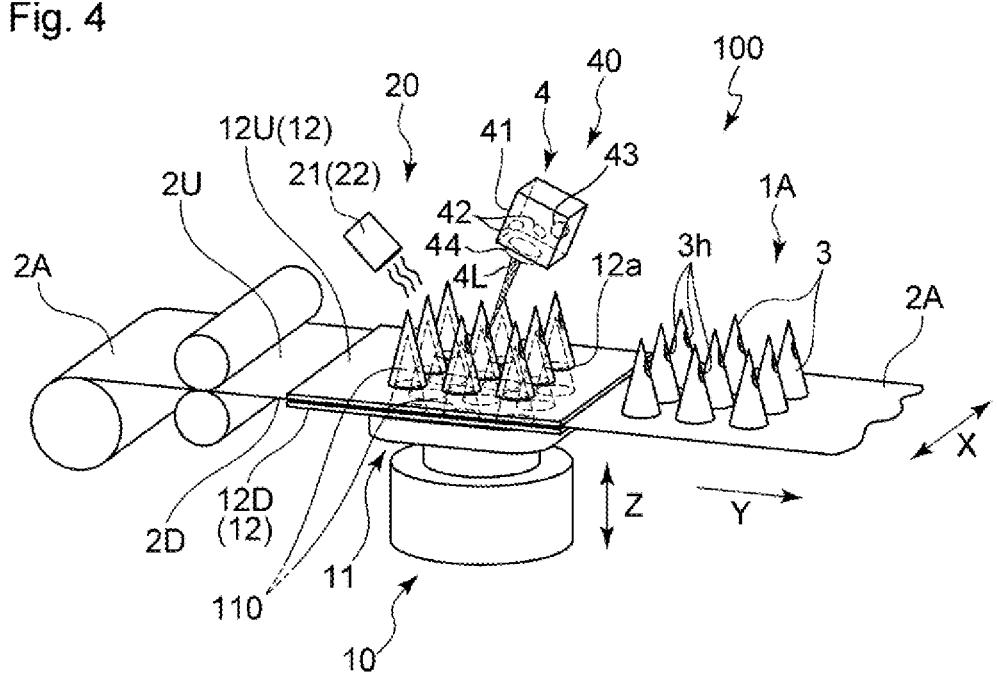
FIG. 4 shows the overall configuration of a manufacturing apparatus for manufacturing the hollow protruding implement shown in FIG. 1 according to a preferred embodiment.

Next, a method for manufacturing the hollow protruding implement of the present invention will be described with reference to FIGS. 4 to 6, using a method for manufacturing the above-described hollow protruding implement 1 as an example. FIG. 4 shows the overall configuration of a manufacturing apparatus 100 according to an embodiment used for implementing the method for manufacturing the hollow protruding implement 1. Note that, although the hollow protrusions 3 in the hollow protruding implement 1 are very small as described above, the hollow protrusions 3 in the hollow protruding implement 1 are illustrated very large in FIG. 4.

As shown in FIG. 4, the manufacturing apparatus 100 includes a protrusion forming section 10 including a projecting mold part 11 for forming hollow protrusions 3 on the base material sheet 2A, and an opening forming section 40 including a contactless opening forming means that forms the openings 3h penetrating the hollow protrusions 3. Also, the manufacturing apparatus 100 includes a cooling section 20. The manufacturing apparatus 100 is configured to insert the projecting mold part 11 into the base material sheet 2A from one face 2D side thereof, thereby forming non-penetrated hollow protrusions 3 that project from another face 2U side of the base material sheet 2A, and to subsequently form the openings 3h, which are through holes, in the non-penetrated hollow protrusions 3 by using the opening forming means from the other face 2U side of the base material sheet 2A. Hereinafter, the method for manufacturing the hollow protruding implement 1 with the use of the manufacturing apparatus 100 will be described in detail.

In the description below, the direction in which the base material sheet 2A is transported is taken as the direction Y, the direction that is orthogonal to the transporting direction and that is the second direction of the base material sheet 2A that is being transported is taken as the direction X, and the thickness direction of the base material sheet 2A that is being transported is taken as a direction Z.

In the method for manufacturing the hollow protruding implement 1 with the use of the manufacturing apparatus 100, first, as shown in FIG. 4, a continuous base material sheet 2A is taken out from a raw material roll of the base material sheet 2A containing a thermoplastic resin, and transported in the transporting direction Y. Then, when the base material sheet 2A is transported to a predetermined position, the transport of the base material sheet 2A is stopped. In this manner, according to the method for manufacturing the hollow protruding implement 1, the continuous base material sheet 2A is transported intermittently.

The base material sheet 2A is a sheet that is formed into the basal member 2 included in the hollow protruding implement 1 that is to be manufactured, and contains a thermoplastic resin. The base material sheet 2A is preferably a sheet mainly made of thermoplastic resin, that is, containing a thermoplastic resin in an amount of 50 mass % or greater, and more preferably a sheet containing a thermoplastic resin in an amount of 90 mass % or greater. Examples of the thermoplastic resin include poly-fatty acid esters, polycarbonate, polypropylene, polyethylene, polyester, polyamide, polyamide imide, polyether ether ketone, polyetherimide, polystyrene, polyethylene terephthalate, polyvinyl chloride, nylon resin, acrylic resin, and combinations thereof. From the viewpoint of biodegradability, poly-fatty acid esters are preferably used. Specific examples of poly-fatty acid esters include polylactic acid, polyglycolic acid, and combinations thereof. Note that the base material sheet 2A may be formed of a mixture including, for example, hyaluronic acid, collagen, starch, cellulose, etc., in addition to thermoplastic resin. The thickness of the base material sheet 2A is similar to the thickness T2 (see FIG. 3) of the basal member 2 included in the hollow protruding implement 1 that is to be manufactured.

Next, in the method for manufacturing the hollow protruding implement 1, as shown in FIG. 4, a protrusion forming step is performed in which the projecting mold part 11 of the protrusion forming section 10 is inserted into the continuous base material sheet 2A from the face 2D side thereof to thereby form fine hollow protrusions 3 projecting from the other face 2U side of the base material sheet 2A.

As shown in FIG. 4, the protrusion forming section 10 includes the protrusion-forming projecting mold part 11. The projecting mold part 11 may or may not be provided with a heating means (not shown), but, in the manufacturing apparatus 100, the projecting mold part 11 is provided with a heating means (not shown).

Moreover, in the manufacturing apparatus 100, no heating means needs to be provided in addition to the heating means of the projecting mold part 11. In this specification, "no heating means needs to be provided in addition to the heating means of the projecting mold part 11" means not only cases in which other heating means are completely excluded but also cases in which a means for heating the base material sheet 2A to a temperature below its softening temperature, or preferably below its glass transition temperature is included. Note that it is however preferable that no other heating means are included at all.

The projecting mold part 11 refers to a member having projections 110, which are portions to be inserted into the base material sheet 2A, and, in the manufacturing apparatus 100, the projecting mold part 11 is disposed on a disc-shaped base portion. However, the present invention is not limited to this structure, and the projecting mold part 11 may be formed only from projections 110 or may have a structure in which a plurality of projections 110 are arranged on a stand-like support. The projecting mold part 11 has projections 110 that match the number of hollow protrusions 3 in the hollow protruding implement 1 to be manufactured, the arrangement of the hollow protrusions 3, and the general outer shape of the hollow protrusions 3, and, in the manufacturing apparatus 100, nine conical projections 110 are provided corresponding to the nine conical hollow protrusions 3.

As shown in FIG. 4, the nine projections 110 are each formed in a conical shape with a sharp tip, and are arranged with their tips facing upward in the thickness direction Z. The projecting mold part 11 is disposed on the face 2D side (lower face side) of the base material sheet 2A while being spaced apart downward in the thickness direction Z from that face 2D by a certain distance. The projecting mold part 11 can be moved vertically in the thickness direction Z by an electric actuator (not shown). The tips of the projections 110 of the projecting mold part 11 can be brought into contact with the face 2D of the base material sheet 2A.

In the manufacturing apparatus 100, the heating means of the projecting mold part 11 is an ultrasonic vibration device. It is preferable that the operation to generate ultrasonic vibrations of the projecting mold part 11 is performed from immediately before the projecting mold part 11 comes into contact with the base material sheet 2A to immediately before the procedure reaches the next step, that is, the cooling step, which will be described later.

The operation of the projecting mold part 11 as well as the heating conditions of the heating means included in the projecting mold part 11, such as the operation of the heating means of the projecting mold part 11, are controlled by a control means (not shown) included in the manufacturing apparatus 100.

With regard to the ultrasonic vibrations generated by the ultrasonic vibration device of the projecting mold part 11, in order to form hollow protrusions 3, the frequency thereof is preferably 10 kHz or greater, and more preferably 15 kHz or greater, is preferably 50 kHz or less, and more preferably 40 kHz or less, and, specifically, is preferably from 10 to 50 kHz, and more preferably from 15 to 40 kHz. Moreover, with regard to the ultrasonic vibrations of the projecting mold part 11, in order to form hollow protrusions 3, the amplitude thereof is preferably 1 µm or greater, and more preferably 5 µm or greater, is preferably 60 µm or less, and more preferably 50 µm or less, and, specifically, is preferably from 1 to 60 µm, and more preferably from 5 to 50 µm.

It is sufficient that the shape of the projecting mold part 11 on the tip side thereof corresponds to the outer shape of the hollow protrusions 3 included in the hollow protruding implement 1 to be manufactured. The projections 110 of the projecting mold part 11 are formed with a height that is equal to or slightly higher than the projecting height H1 (see FIG. 3) of the hollow protrusions 3 included in the hollow protruding implement 1 to be manufactured, and this height is preferably 0.01 mm or greater, and more preferably 0.02 mm or greater, is preferably 30 mm or less, and more preferably 20 mm or less, and, specifically, is preferably from 0.01 to 30 mm, and more preferably from 0.02 to 20 mm. The projections 110 of the projecting mold part 11 each have a tip diameter D1 (see FIG. 5) that is preferably 0.001 mm or greater, and more preferably 0.005 mm or greater, is preferably 1 mm or less, and more preferably 0.5 mm or less, and, specifically, is preferably from 0.001 to 1 mm, and more preferably from 0.005 to 0.5 mm. The tip diameter D1 of the projections 110 of the projecting mold part 11 is measured as follows.

The projections 110 of the projecting mold part 11 each have a base diameter D2 that is preferably 0.1 mm or greater, and more preferably 0.2 mm or greater, is preferably 5 mm or less, and more preferably 3 mm or less, and, specifically, is preferably from 0.1 to 5 mm, and more preferably from 0.2 to 3 mm. The projections 110 of the projecting mold part 11 each have a tip angle $\alpha$ that is preferably 1 degree or greater, and more preferably 5 degrees or greater, in order to facilitate making the projections 110 sufficiently strong. Furthermore, in order to obtain hollow protrusions 3 with an appropriate angle, the tip angle $\alpha$ is preferably 60 degrees or less, and more preferably 45 degrees or less, and, specifically, is preferably from 1 to 60 degrees, and more preferably from 5 to 45 degrees. The tip angle $\alpha$ of the projecting mold part 11 is measured as follows.

Measurement of Tip Diameter of Projections 110 of Projecting Mold Part 11

The tip portion of a projection 110 of the projecting mold part 11 is magnified at a predetermined magnification and observed using a scanning electron microscope (SEM) or a microscope. Next, as shown in FIG. 5, an imaginary straight line ILc is extended along the straight-line portion of one lateral side 11a of two lateral sides 11a and 11b, and an imaginary straight line ILd is extended along the straight-line portion of the other lateral side 11b. Then, a point where the lateral side 11a separates from the imaginary straight line ILc on the tip side is obtained as a first tip point 11a1, and a point where the other lateral side 11b separates from the imaginary straight line ILd is obtained as a second tip point 11b1. A length D1 of a straight line that links the thus obtained first tip point 11a1 and second tip point 11b1 is measured using a scanning electron microscope or a microscope, and the measured length of the straight line is taken as the tip diameter of the projection 110.

Measurement of Tip Angle α of Projections 110 of Projecting Mold Part 11

Figure 5:
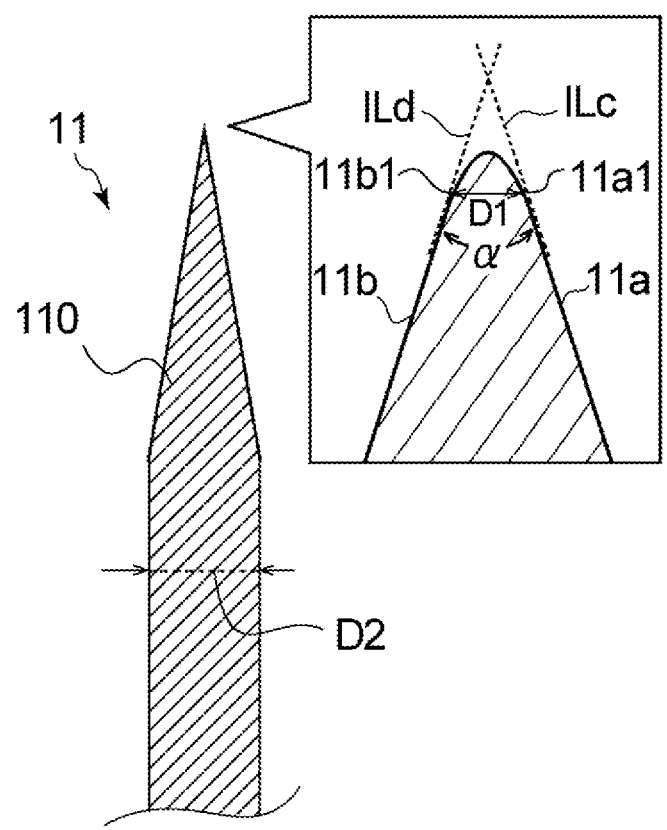
FIG. 5 is an explanatory diagram illustrating a method for measuring the tip diameter and the tip angle of a projection of a projecting mold part.

The tip portion of a projection 110 of the projecting mold part 11 is magnified at a predetermined magnification using a scanning electron microscope or a microscope and observed like the image shown in FIG. 5, for example. Next, as shown in FIG. 5, an imaginary straight line ILc is extended along the straight-line portion of one lateral side 11a of two lateral sides 11a and 11b, and an imaginary straight line ILd is extended along the straight-line portion of the other lateral side 11b. An angle formed by the imaginary straight line ILc and the imaginary straight line ILd is measured using a scanning electron microscope or a microscope, and the measured angle is taken as the tip angle α of the projection 110 of the projecting mold part 11.

The projecting mold part 11 is made of a high-strength material that is unlikely to break. Examples of the material for forming the projecting mold part 11 include metals, such as steel, stainless steel, aluminum, an aluminum alloy, nickel, a nickel alloy, cobalt, a cobalt alloy, copper, a copper alloy, beryllium copper, and a beryllium copper alloy, and ceramics.

As shown in FIG. 4, the protrusion forming section 10 has a first opening plate 12U serving as a bending suppressing means on the other face 2U side (upper face side) of the base material sheet 2A, and has a second opening plate 12D serving as a bending suppressing means on the face 2D side (lower face side) of the base material sheet 2A. The opening plates 12U and 12D are constituted by plate-like members that extend parallel to the transporting direction Y. The opening plates 12U and 12D sandwich the base material sheet 2A therebetween at regions thereof other than opening portions 12a.

Each of the opening plates 12U and 12D may be formed such that a single opening portion 12a has a greater opening area than the cross-sectional area of the projections 110 of the projecting mold part 11 so as to allow a plurality of projections 110 to pass through, but, in the manufacturing apparatus 100, as shown in FIGS. 4 and 6, the opening plates 12U and 12D are formed such that one opening portion 12a allows one projection 110 to pass through. In the manufacturing apparatus 100, the opening portions 12a of the first opening plate 12U are arranged concentrically with the respective opening portions 12a of the second opening plate 12D. Accordingly, every pair of opening portions 12a of the first opening plate 12U and the second opening plate 12D sandwiching the base material sheet 2A therebetween overlap each other in the thickness direction.

The opening plates 12U and 12D are movable in directions closer to and away from the base material sheet 2A. In the manufacturing apparatus 100, each of the opening plates 12U and 12D can be moved vertically in the thickness direction Z by the electric actuator (not shown). The operation of the opening plates 12U and 12D is controlled by a control means (not shown) included in the manufacturing apparatus 100.

Although the opening plates 12U and 12D of the manufacturing apparatus 100 are movable in directions closer to and away from the base material sheet 2A, the second opening plate 12D does not need to be movable in directions closer to and away from the base material sheet 2A.

The material for forming a support 12 (the opening plates 12U and 12D) may be the same as the material for forming the projecting mold part 11, and examples thereof include a synthetic resin and the like.

In the method for manufacturing the hollow protruding implement 1, as shown in FIGS. 6(a) and 6(b), the protrusion forming step is performed in a state in which the base material sheet 2A is sandwiched between the first opening plate 12U and the second opening plate 12D. In the protrusion forming step, the projections 110 are made to pass through the opening portions 12a of the second opening plate 12D from the face 2D side of the base material sheet 2A, and, while the projections 110 are preliminarily ultrasonically vibrated by the ultrasonic vibration device as shown in FIG. 6(a), the projecting mold part 11 is then brought into contact with the face 2D of the base material sheet 2A. Thus, contact portions TP are softened. Subsequently, as shown in FIG. 6(b), while the contact portions TP are softened, the projections 110 are moved upward from the face 2D side toward the other face 2U side of the base material sheet 2A, and the projections 110 are inserted into the base material sheet 2A while bending of the base material sheet 2A is suppressed by the first opening plate 12U, which is disposed on the other face 2U side of the base material sheet 2A. Then, non-penetrated fine hollow protrusions 3 projecting from the other face 2U side of the base material sheet 2A are formed.

In order to form hollow protrusions 3, the heating temperature to which the base material sheet 2A is heated by the projecting mold part 11 is preferably equal to or higher than the glass transition temperature of the base material sheet 2A that is used and below the melting temperature thereof, and is especially preferably equal to or higher than the softening temperature thereof and below the melting temperature thereof. More specifically, the heating temperature is preferably 30° C. or greater, and more preferably 40° C. or greater, is preferably 300° C. or less, and more preferably 250° C. or less, and, specifically, is preferably from 30° C. to 300° C., and more preferably from 40° C. to 250° C. Note that in the case where the base material sheet 2A is heated using the ultrasonic vibration device, the heating temperature is applied as the temperature range of those portions of the base material sheet 2A that are in contact with the projections 110. On the other hand, in the case where the base material sheet 2A is heated using a heater device instead of an ultrasonic vibration device, the heating temperature of the projecting mold part 11 can be adjusted within the above-described range. Note that the glass transition temperature (Tg) is measured according to the following measurement method, and the softening temperature is measured according to JIS K-7196 "Testing method for softening temperature of thermoplastic film and sheeting by thermomechanical analysis".

Method for Measuring Glass Transition Temperature (Tg)

The glass transition temperature is determined by measuring the heat quantity by using a DSC measurement device. More specifically, the measurement device used is a differential scanning calorimeter (Diamond DSC) from Perkin Elmer. A 10-mg test piece is sampled from the base material sheet. As for the measurement conditions, the temperature is kept constant at 20° C. for 5 minutes, and then the temperature is raised from 20° C. to 320° C. at a rate of 5° C./minute, to obtain a DSC curve wherein the horizontal axis indicates temperature and the vertical axis indicates heat quantity. The glass transition temperature Tg is determined from the DSC curve.

Note that the "glass transition temperature (Tg) of the base material sheet" refers to the glass transition temperature (Tg) of the resin constituting the base material sheet. In cases where there are a plurality of types of constituent resins and the glass transition temperatures (Tg) of the plurality of types of resins are different from each other, the heating temperature to which the base material sheet is heated by the heating means is preferably at least equal to or higher than the lowest glass transition temperature (Tg) among the plurality of glass transition temperatures (Tg), and more preferably equal to or higher than the highest glass transition temperature (Tg) among the plurality of glass transition temperatures (Tg).

The same applies to the "softening temperature of the base material sheet", as with the glass transition temperature (Tg). In cases where there are a plurality of types of constituent resins in the base material sheet and the softening temperatures of the plurality of types of resins are different from each other, the heating temperature to which the base material sheet is heated by the heating means is preferably at least equal to or higher than the lowest softening temperature among the plurality of softening temperatures, and more preferably equal to or higher than the highest softening temperature among the plurality of softening temperatures.

In cases where the base material sheet includes two or more types of resins having different melting points, the heating temperature to which the base material sheet is heated by the heating means is preferably below the lowest melting point among the plurality of melting points.

If the insertion speed at which the projecting mold part 11 is inserted into the base material sheet 2A is too slow, the resin is excessively heated and softened, whereas, if the insertion speed is too fast, heating and softening are insufficient. Thus, in order to efficiently form the hollow protrusions 3, the insertion speed is preferably 0.1 mm/sec or greater, and more preferably 1 mm/sec or greater, is preferably 1,000 mm/sec or less, and more preferably 800 mm/sec or less, and, specifically, is preferably from 0.1 to 1,000 mm/sec, and more preferably from 1 to 800 mm/sec. Overheating will result if the softening time that is the time from when upward movement of the projecting mold part 11 in a heated state is stopped until when the cooling step, which is the next step, is performed while keeping the projecting mold part 11 inserted in the interiors of the hollow protrusions 3 is too long, but in order to compensate for insufficient heating, the softening time is preferably 0 seconds or greater, and more preferably 0.1 seconds or greater, is preferably 10 seconds or less, and more preferably 5 seconds or less, and, specifically, is preferably from 0 to 10 seconds, and more preferably from 0.1 to 5 seconds.

The insertion height by which the projecting mold part 11 is inserted into the base material sheet 2A is preferably 0.01 mm or greater, and more preferably 0.02 mm or greater, is preferably 10 mm or less, and more preferably 5 mm or less, and, specifically, is preferably from 0.01 to 10 mm, and more preferably from 0.02 to 5 mm, in order to efficiently form the hollow protrusions 3. Here, "insertion height" refers to the distance between the apex of a projection 110 and the other face 2U (upper face) of the base material sheet 2A in a state in which the projection 110 of the projecting mold part 11 is inserted furthest into the base material sheet 2A. Accordingly, the insertion height in the protrusion forming step refers to the distance from the other face 2U to the apex of a projection 110 as measured in the perpendicular direction in a state in which the projection 110 has been inserted to the deepest position and projects from the other face 2U of the base material sheet 2A.

Next, in the method for manufacturing the hollow protruding implement 1, as shown in FIGS. 4 and 6(c), the cooling step of cooling the hollow protrusions 3 is performed using a cold air blowing device 21 included in the cooling section 20. As shown in FIG. 4, in the cold air blowing device 21, an air vent 22 for blowing cold air is disposed on the other face 2U side (the upper face side) of the base material sheet 2A, and the non-penetrated hollow protrusions 3 are cooled by cold air blown from the air vent 22. Note that a configuration is also possible in which a cold air blowing device has a hollow shape that covers the entire other face 2U side (the upper face side) and the entire face 2D side (the lower face side) of the continuous base material sheet 2A that is being transported, and the continuous base material sheet 2A is transported in the transporting direction (direction Y) through the cold air blowing device, wherein, for example, an air vent 22 for blowing cold air is provided in the hollow space of the cold air blowing device. The cooling temperature and the cooling time of the cold air blowing device 21 are controlled by a control means (not shown) included in the manufacturing apparatus 100.

In the method for manufacturing the hollow protruding implement 1, as shown in FIG. 6(c), the cooling step of cooling the non-penetrated hollow protrusions 3 is performed in a state in which the projecting mold part 11 is inserted in the interiors of the non-penetrated hollow protrusions 3. In the cooling step, in a state in which the movement of the projecting mold part 11 in the thickness direction (direction Z) by the electric actuator (not shown) is stopped, and the projections 110 of the projecting mold part 11 are inserted in the interiors of the non-penetrated hollow protrusions 3, cooling is performed by blowing cold air from the air vent 22 disposed on the other face 2U side (the upper face side) of the base material sheet 2A, while keeping the projections 110 inserted in the interiors of the non-penetrated hollow protrusions 3. Note that, when performing cooling, generation of ultrasonic vibrations by the ultrasonic vibration device of the projecting mold part 11 may be continued or stopped, but in order to keep the shape of the non-penetrated hollow protrusions 3 constant without it excessively changing, the generation of ultrasonic vibrations is preferably stopped.

The temperature of the cold air to be blown is preferably $-50°$ C. or greater, and more preferably $-40°$ C. or greater, is preferably $26°$ C. or less, and more preferably $10°$ C. or less, and, specifically, is preferably from $-50°$ C. to $26°$ C., and more preferably from $-40°$ C. to $10°$ C., in order to form the non-penetrated hollow protrusions 3.

The cooling time for cooling by blowing cold air is preferably 0.01 seconds or greater, and more preferably 0.5 seconds or greater, is preferably 60 seconds or less, and more preferably 30 seconds or less, and, specifically, is preferably from 0.01 to 60 seconds, and more preferably from 0.5 to 30 seconds, in order to balance moldability and processing time.

Note that in the case where the heating means of the projecting mold part 11 employs ultrasonic vibrations as in the manufacturing apparatus 100, it is not necessary to provide the cold air blowing device 21, and it is also possible to perform cooling by turning off vibrations of the ultrasonic vibration device. In this respect, it is preferable to use ultrasonic vibrations as the heating means, because the apparatus can be simplified and it is also easy to manufacture the hollow protruding implement 1 at high speed. Moreover, since heat is less likely to be transmitted to portions of the base material sheet 2A that are not in contact with the projecting mold part 11, and the cooling is efficiently performed by turning off the application of ultrasonic vibrations, deformation in portions other than the portions to be molded is advantageously unlikely to occur.

In the method for manufacturing the hollow protruding implement 1, the opening forming step of forming the openings 3h is performed while the non-penetrated hollow protrusions 3 are being cooled in the cooling step, or after the end of the cooling step. In the manufacturing method shown in FIGS. 4 and 6, the openings 3h, which are through holes, are formed in the non-penetrated hollow protrusions 3 by applying electromagnetic waves or hot air to the non-penetrated hollow protrusions 3 with the use of the contactless opening forming means included in the opening forming section 40, while cooling the non-penetrated hollow protrusions 3. If the openings 3h are formed in the hollow protrusions 3 while the non-penetrated hollow protrusions 3 are being cooled in this manner, the cooling step and the opening forming step can be performed simultaneously, and therefore the manufacturing time can be shortened.

The opening forming section 40 includes the contactless opening forming means on the other face 2U side of the base material sheet 2A. Examples of the contactless opening forming means include machining devices that use a heat source, such as a laser device for irradiating laser light, a hot air ejection device for ejecting hot air, and a halogen lamp irradiation device for irradiating infrared rays. In the manufacturing apparatus 100, a laser device 4 is used in view of the light collecting properties and the high-precision energy control capability that are necessary for micromachining. As shown in FIG. 4, the laser device 4 has an irradiation head 41, which is a galvano scanner capable of freely scanning laser light 4L. The irradiation head 41 is disposed on the other face 2U side (upper face side) of the base material sheet 2A while being spaced apart upward in the thickness direction Z from the other face 2U by a certain distance. If the openings 3h are formed in the hollow protrusions 3 by irradiating the non-penetrated hollow protrusions 3 with the laser light 4L from the irradiation head 41 that is disposed on the other face 2U side (upper face side) of the base material sheet 2A in this manner, burrs are unlikely to be formed around the openings 3h on the outer surfaces 32 of the hollow protrusions 3. Moreover, the openings 3h are easily formed at any desired positions of the hollow protrusions 3, and the positions of the openings 3h relative to the skin surface to which it is desired to deliver a liquid agent or the like are therefore easily adjusted as desired.

As shown in FIG. 4, the irradiation head 41 has a lens 43 for collecting the irradiated laser light 4L, as well as two mirrors 42 and a protective lens 44 for freely scanning the collected laser light 4L. The protective lens 44 may or may not be provided, but in order to prevent dirt and dust from entering the optical system, it is preferred that the protective lens 44 is provided. The mirrors 42 are attached to a motor shaft. The mirrors 42 include a mechanism for moving an irradiation point at which the laser light 4L is incident on a hollow protrusion 3 on the base material sheet 2A in the transporting direction Y of the base material sheet 2A and a mechanism for moving the irradiation point in the direction X that is orthogonal to the transporting direction of the base material sheet 2A, and are configured to be able to freely scan the laser light 4L. The lens 43 is movable in the direction of the optical axis and includes a mechanism for collecting the laser light 4L and keeping the spot diameter at the irradiation point at which the laser light 4L is incident on a hollow protrusion 3 constant, a mechanism for moving the irradiation point of the laser light 4L in the thickness direction (direction Z) of the base material sheet 2A, and the like. The irradiation head 41, which has the mirrors 42 and the lens 43, is configured to be able to adjust the irradiation point of the laser light 4L three-dimensionally, that is, in the direction X, the direction Y, and the direction Z. Therefore, a position that is desired to be irradiated on each hollow protrusion 3 can be irradiated with the laser light 4L with a predetermined spot diameter by determining the three-dimensional coordinates of the position that is desired to be irradiated for each of the nine hollow protrusions 3. Preferably, laser light that can be absorbed in the hollow protrusions 3 where openings are to be formed is used as the laser light 4L. When the base material sheet 2A on which the hollow protrusions 3 are formed is a sheet, such as a film, mainly made of a thermoplastic resin, it is preferable that a $CO_2$ laser, an excimer laser, an argon laser, a YAG laser, an LD laser (semiconductor laser), a $YVO_4$ laser, a fiber laser, or the like is used for the laser light 4L.

In the method for manufacturing the hollow protruding implement 1, as shown in FIG. 6(c), in a state in which the projecting mold part 11 is inserted in the interiors of the non-penetrated hollow protrusions 3, the individual non-penetrated hollow protrusions 3 are irradiated with the laser light 4L from the irradiation head 41 while the hollow protrusions 3 are being cooled, and thus, the openings 3h are formed. If the openings 3h are formed by irradiating the laser light 4L in a state in which the projecting mold part 11 is inserted in the interiors of the non-penetrated hollow protrusions 3 as described above, burrs are unlikely to be formed around the openings 3h on the inner surfaces 31 of the hollow protrusions 3, and thus, it is possible to stably deliver agents into the skin. Moreover, if the openings 3h are formed by irradiating the laser light 4L in a state in which the projecting mold part 11 is inserted in the interiors of the non-penetrated hollow protrusions 3, the inner surfaces 31 of side walls of the hollow protrusions 3 that are opposite to side walls irradiated with the laser light 4L are unlikely to be damaged, and thus, it is possible to stably deliver agents into the skin.

The openings 3h may be formed at the tips of the hollow protrusions 3, but, in the opening forming step, it is preferable to form the openings 3h by irradiating positions offset from the centers of the tip portions of the non-penetrated hollow protrusions 3 with the laser light 4L, because this configuration makes it unlikely for the tips of the hollow protrusions 3 to be damaged, and also makes it easy to pierce the skin. From the viewpoint of forming the openings 3h by irradiating the side walls of the hollow protrusions 3 with the laser light 4L with a small amount of irradiation energy, and the viewpoint of suppressing the effect of the irradiation energy of the laser light 4L and maintaining the strength around the openings 3h that are formed, in the opening forming step, as shown in FIG. 6(c), it is preferable to form the openings 3h by irradiating the laser light 4L from the irradiation head 41 of the laser device 4 onto the non-penetrated hollow protrusions 3 from a direction ILf that is inclined with respect to an insertion direction ILe of the projections 110 of the projecting mold part 11. From the same viewpoints, the angle θ that is formed by the insertion direction ILe of the projections 110 and the inclined direction ILf in which the laser light 4L is irradiated is preferably 5 degrees or greater, more preferably 10 degrees or greater, and even more preferably 15 degrees or greater, and is preferably 85 degrees or less, more preferably 80 degrees or less, and even more preferably 75 degrees or less. Specifically, the angle θ is preferably from 5 to 85 degrees, more preferably from 10 to 80 degrees, and even more preferably from 15 to 75 degrees. From the same viewpoints, the irradiation time of the laser light 4L is preferably 0.001 ms or longer, and more preferably 0.005 ms or longer, is preferably 5 ms or less, and more preferably 3 ms or less, and, specifically, is preferably from 0.001 to 5 ms, and more preferably from 0.005 to 3 ms. Moreover, from the same viewpoints, the laser output of the laser light 4L is preferably 0.5 W or greater, and more preferably 1 W or greater, is preferably 100 W or less, and more preferably 50 W or less, and, specifically, is preferably from 0.5 to 100 W, and more preferably from 1 to 50 W.

Then, as shown in FIG. 6(d), in a state in which the projecting mold part 11 is inserted in the interiors of the non-penetrated hollow protrusions 3, the openings 3h are formed in the non-penetrated hollow protrusions 3, and cooling of the hollow protrusions 3 is stopped. Next, as shown in FIG. 6(e), a release step is performed in which the projecting mold part 11 is released from the interiors of the hollow protrusions 3 in which the openings 3h are formed, to thereby form hollow protrusions 3 having hollow interiors. If the generation of ultrasonic vibrations by the ultrasonic vibration device of the projecting mold part 11 is continued in the cooling step, it is preferable to stop the generation of ultrasonic vibrations in the release step. In the release step, the projecting mold part 11 is moved downward in the thickness direction (direction Z) by the electric actuator (not shown), and the projections 110 are released from the state in which the projections 110 are inserted in the interiors of the respective hollow protrusions 3, so that hollow protrusions 3 respectively having hollow interiors are formed. In the release step, the projections 110 are easily released from the interiors of the hollow protrusions 3 because the second opening plate 12D is used as the bending suppressing means that suppresses bending of the base material sheet 2A during releasing of the projecting mold part 11 from the interiors of the hollow protrusions 3. In the method for manufacturing the hollow protruding implement 1, a precursor 1A of the hollow protruding implement 1 in which nine hollow protrusions 3 are formed in an array on the other face 2U (upper face) of the base material sheet 2A can be produced. After the precursor 1A of the hollow protruding implement 1 is produced, the first opening plate 12U and the second opening plate 12D are separated from the base material sheet 2A, and the sandwiched state of the base material sheet 2A is cancelled.

The thus formed precursor 1A of the hollow protruding implement 1 is then transported downstream in the transporting direction Y. Then, the precursor 1A is cut in a predetermined range in a cutting step, and thus a hollow protruding implement 1 having a sheet-like basal member 2 and a plurality of hollow protrusions 3, such as the one shown in FIG. 1, can be manufactured. Hollow protruding implements 1 can be continuously and efficiently manufactured by repeating the above-described steps.

Note that the hollow protruding implement 1 manufactured as described above may be further shaped into a predetermined shape in subsequent steps, or the shape of the base material sheet 2A may be adjusted in advance into a desired shape before the step of inserting the projecting mold part 11.

As described above, the manufacturing method of the present embodiment that uses the manufacturing apparatus 100 for manufacturing the hollow protruding implement 1 includes the protrusion forming step of inserting the projecting mold part 11 into the base material sheet 2A from the face 2D side thereof, thereby forming the non-penetrated fine hollow protrusions 3 projecting from the other face 2U side of the base material sheet 2A, as well as the opening forming step of irradiating the non-penetrated hollow protrusions 3 with the laser light 4L from the laser device 4, which is the contactless opening forming means disposed on the other face 2U side of the base material sheet 2A, thereby forming the openings 3h. Therefore, the fine hollow protrusions 3 having the openings 3h can be formed with a precise shape, and burrs are unlikely to be formed around the openings 3h on the outer surfaces 32 of the hollow protrusions 3. The thus manufactured hollow protruding implement 1 is capable of easily piercing the skin and enables stable delivery of agents into the skin.

Although the present invention has been described based on preferred embodiments above, the present invention is not limited to the foregoing embodiments, and may be changed as appropriate.

For example, in the above-described method for manufacturing the hollow protruding implement 1, in a state in which the projecting mold part 11 is inserted in the interiors of the non-penetrated hollow protrusions 3, and while the hollow protrusions 3 are being cooled in the cooling step, the openings 3h that penetrate the hollow protrusions 3 are formed using the contactless opening forming means, but alternatively, the openings 3h that penetrate the non-penetrated hollow protrusions 3 may be formed using the contactless opening forming means after the projecting mold part 11 is released from the interiors of the non-penetrated hollow protrusions 3. Specifically, as shown in FIGS. 7(a) and 7(b), in a state in which the base material sheet 2A is sandwiched between the first opening plate 12U and the second opening plate 12D, the projections 110 are made to pass through the opening portions 12a in the second opening plate 12D from the face 2D side of the base material sheet 2A, and while the projections 110 are preliminarily ultrasonically vibrated by the ultrasonic vibration device, the projecting mold part 11 is brought into contact with the face 2D of the base material sheet 2A. While the contact portions TP are softened in this manner, the projections 110 are moved upward from the face 2D side toward the other face 2U side of the base material sheet 2A, and thus, the non-penetrated hollow protrusions 3 projecting from the other face 2U side of the base material sheet 2A are formed.

Next, as shown in FIG. 7(c), the non-penetrated hollow protrusions 3 are cooled using the cold air blowing device 21 disposed on the other face 2U side (upper face side) of the base material sheet 2A. Then, the release step of releasing the projecting mold part 11 from the interiors of the non-penetrated hollow protrusions 3 and thereby forming the hollow protrusions 3 having hollow interiors is performed. In the release step, the generation of ultrasonic vibrations by the ultrasonic vibration device of the projecting mold part 11 is stopped, the projecting mold part 11 is moved downward in the thickness direction (direction Z) by the electric actuator (not shown), the projections 110 are released from the interiors of the hollow protrusions 3 while bending of the base material sheet 2A is suppressed by the second opening plate 12D, and thus, the non-penetrated hollow protrusions 3 are formed.

Next, as shown in FIG. 7(d), after cooling, the openings 3h are formed by irradiating the non-penetrated hollow protrusions 3 with the laser light 4L from the irradiation head 41 of the laser device 4 disposed on the other face 2U side (upper face side) of the base material sheet 2A, and thus the hollow protrusions 3 in which the openings 3h are formed may be formed as shown in FIG. 7(e).

Although the above-described method for manufacturing the hollow protruding implement 1 uses the ultrasonic vibration device as the heating means of the projecting mold part 11, a heater device may also be used as the heating means of the projecting mold part 11.

With regard to the above-described embodiments, the present invention further discloses the following methods for manufacturing a hollow protruding implement having an opening.

<1> A method for manufacturing a hollow protruding implement including a fine hollow protrusion having an opening, the method comprising:

a protrusion forming step of inserting a protrusion-forming projecting mold part into a base material sheet from one face side thereof, the base material sheet containing a thermoplastic resin, thereby forming a non-penetrated hollow protrusion projecting from another face side of the base material sheet; and an opening forming step of forming an opening as a through hole in the non-penetrated hollow protrusion by using a contactless opening forming means disposed on the other face side of the base material sheet.

<2> The method for manufacturing a hollow protruding implement as set forth in clause 1, wherein, in the opening forming step, the opening is formed in a state in which the projecting mold part is inserted in an interior of the non-penetrated hollow protrusion.

<3> The method for manufacturing a hollow protruding implement as set forth in clause 1 or 2, wherein, in the opening forming step, the opening is formed at a position offset from a center of a tip portion of the non-penetrated hollow protrusion.

<4> The method for manufacturing a hollow protruding implement as set forth in any one of clauses 1 to 3, wherein a laser device is used as the contactless opening forming means.

<5> The method for manufacturing a hollow protruding implement as set forth in clause 4, wherein, in the opening forming step, the opening is formed by irradiating laser light from the laser device onto the non-penetrated hollow protrusion from a direction that is inclined with respect to an insertion direction of the projecting mold part.

<6> The method for manufacturing a hollow protruding implement as set forth in clause 5, wherein an angle that is formed by the insertion direction of the projecting mold part and the inclined direction in which the laser light is irradiated is preferably 5 degrees or greater, more preferably 10 degrees or greater, and even more preferably 15 degrees or greater, and is preferably 85 degrees or less, more preferably 80 degrees or less, and even more preferably 75 degrees or less, and specifically, is preferably from 5 to 85 degrees, more preferably from 10 to 80 degrees, and even more preferably from 15 to 75 degrees.

<7> The method for manufacturing a hollow protruding implement as set forth in any one of clauses 1 to 6, wherein the projecting mold part has a heating means, and in the protrusion forming step, the base material sheet is heated and softened by the heating means.

<8> The method for manufacturing a hollow protruding implement as set forth in clause 7, wherein a time for which the base material sheet is heated and softened by the heating means is preferably 0 seconds or greater, and more preferably 0.1 seconds or greater, is preferably 10 seconds or less, and more preferably 5 seconds or less, and, specifically, is preferably from 0 to 10 seconds, and more preferably from 0.1 to 5 seconds.

<9> The method for manufacturing a hollow protruding implement as set forth in any one of clauses 1 to 8, wherein the projecting mold part has a heating means, and an ultrasonic vibration device is used as the heating means.

<10> The method for manufacturing a hollow protruding implement as set forth in any one of clauses 1 to 9, wherein, in the protrusion forming step, an insertion speed at which the projecting mold part is inserted into the base material sheet is preferably 0.1 mm/sec or greater, and more preferably 1 mm/sec or greater, is preferably 1,000 mm/sec or less, and more preferably 800 mm/sec or less, and, specifically, is preferably from 0.1 to 1,000 mm/sec, and more preferably from 1 to 800 mm/sec.

<11> The method for manufacturing a hollow protruding implement as set forth in any one of clauses 1 to 10, comprising:

a cooling step of cooling the non-penetrated hollow protrusion, the cooling step being performed after the protrusion forming step.

<12> The method for manufacturing a hollow protruding implement as set forth in clause 11, wherein, in the cooling step, the non-penetrated hollow protrusion is cooled in a state in which the projecting mold part is inserted in an interior of the non-penetrated hollow protrusion.

<13> The method for manufacturing a hollow protruding implement as set forth in clause 11 or 12, wherein the opening forming step is performed while the non-penetrated hollow protrusion is being cooled in the cooling step, or after the end of the cooling step.

<14> An apparatus for manufacturing a hollow protruding implement including a fine hollow protrusion having an opening, the apparatus comprising:

a protrusion forming section including a protrusion-forming projecting mold part that is disposed on one face side of a base material sheet containing a thermoplastic resin; and an opening forming section including a contactless opening forming means that is disposed on another face side of the base material sheet, wherein the apparatus is configured to insert the projecting mold part into the base material sheet from the one face side thereof, thereby forming a non-penetrated hollow protrusion projecting from the other face side of the base material sheet, and to subsequently form an opening as a through hole in the non-penetrated hollow protrusion by using the opening forming means from the other face side of the base material sheet.

<15> The apparatus for manufacturing a hollow protruding implement as set forth in clause 14, wherein the opening forming section is configured to form the opening in a state in which the projecting mold part is inserted in an interior of the non-penetrated hollow protrusion.

<16> The apparatus for manufacturing a hollow protruding implement as set forth in clause 14 or 15, wherein the opening forming section is configured to form the opening at a position offset from a center of a tip portion of the non-penetrated hollow protrusion.

<17> The apparatus for manufacturing a hollow protruding implement as set forth in any one of clauses 14 to 16, wherein the contactless opening forming means is a laser device.

<18> The apparatus for manufacturing a hollow protruding implement as set forth in clause 17, wherein the opening forming section forms the opening by irradiating laser light from the laser device onto the non-penetrated hollow protrusion from a direction that is inclined with respect to an insertion direction of the projecting mold part.

<19> The apparatus for manufacturing a hollow protruding implement as set forth in clause 18, wherein an angle that is formed by the insertion direction of the projecting mold part and the inclined direction in which the laser light is irradiated is preferably 5 degrees or greater, more preferably 10 degrees or greater, and even more preferably 15 degrees or greater, and is preferably 85 degrees or less, more preferably 80 degrees or less, and even more preferably 75 degrees or less, and specifically, is preferably from 5 to 85 degrees, more preferably from 10 to 80 degrees, and even more preferably from 15 to 75 degrees.

<20> The apparatus for manufacturing a hollow protruding implement as set forth in any one of clauses 14 to 19, wherein the projecting mold part has a heating means that heats and softens the base material sheet.

<21> The apparatus for manufacturing a hollow protruding implement as set forth in clause 20, the apparatus having an ultrasonic vibration device as the heating means.

<22> The apparatus for manufacturing a hollow protruding implement as set forth in any one of clauses 14 to 21, comprising:

a cooling section that cools the non-penetrated hollow protrusion, the cooling section being disposed downstream of the protrusion forming section in a direction in which the base material sheet is transported.

<23> The apparatus for manufacturing a hollow protruding implement as set forth in clause 22, wherein, in the cooling section, the non-penetrated hollow protrusion is cooled in a state in which the projecting mold part is inserted in an interior of the hollow protrusion.

<24> The apparatus for manufacturing a hollow protruding implement as set forth in clause 22 or 23, wherein the opening is formed by the opening forming section while the non-penetrated hollow protrusion is being cooled by the cooling section, or after the end of the cooling by the cooling section.

<25> A hollow protruding implement including a fine hollow protrusion having an opening, wherein the opening is a through hole disposed at a position offset from a center of a tip portion of the hollow protrusion, and an inner diameter of the opening on an outer surface side of the hollow protrusion is greater than the inner diameter thereof on an inner surface side of the hollow protrusion.

<26> The hollow protruding implement as set forth in clause 25, wherein the inner diameter of the opening gradually increases from the inner surface side of the hollow protrusion toward the outer surface side thereof.

<27> The hollow protruding implement as set forth in clause 25 or 26, wherein the inner diameter of the opening on the inner surface side is preferably 1 µm or greater, and more preferably 5 µm or greater, is preferably 500 µm or less, and more preferably 300 µm or less, and, specifically, is preferably from 1 to 500 µm, and more preferably from 5 to 300 µm.

<28> The hollow protruding implement as set forth in any one of clauses 25 to 27, wherein the inner diameter of the opening on the outer surface side is preferably 1.1 or more times, and more preferably 1.2 or more times, is preferably 15 or less times, and more preferably 10 or less times, and, specifically, is preferably from 1.1 to 15 times, and more preferably from 1.2 to 10 times greater than the inner diameter thereof on the inner surface side.

<29> The hollow protruding implement as set forth in any one of clauses 25 to 28, wherein an opening area of the opening on the outer surface side of the hollow protrusion is larger than the opening area of the opening on the inner surface side of the hollow protrusion.

EXAMPLES

Hereinafter, the present invention will be described in greater detail using examples. However, the scope of the present invention is not limited to the following examples.
(1) Preparation of Projecting Mold Part 11 Included in Manufacturing Apparatus A mold part made of SUS304, which is stainless steel, was prepared as the projecting mold part 11. The projecting mold part 11 had one conical projection 110. The projection 110 had a height (height of a tapered portion) H2 of 2.5 mm, a tip diameter D1 of 15 µm, a base diameter D2 of 0.5 mm, and a tip angle of 11 degrees.
(2) Preparation of Laser Device 4 Included in Manufacturing Apparatus A $CO_2$ laser device was used as the laser device 4, and $CO_2$ laser light with a wavelength of 9.3 µm was irradiated.
(3) Preparation of Base Material Sheet 2A

A continuous sheet made of polylactic acid (PLA; Tg 55.8° C.) with a thickness of 0.3 mm was prepared as the base material sheet 2A.
(4) Formation of Non-Penetrated Hollow Protrusion First, a non-penetrated hollow protrusion 3 was formed following the procedures shown in FIGS. 7(*a*) to 7(*c*). The manufacture conditions were such that the projecting mold part 11 had a frequency of ultrasonic vibrations of 20 kHz and an amplitude of ultrasonic vibrations of 40 µm. Furthermore, the projecting mold part 11 had an insertion height of 0.7 mm and an insertion speed of 10 mm/sec. Furthermore, the softening time was 0.1 seconds, and the cooling time was 0.5 seconds. The hollow protrusion 3 formed had a projecting height H1 of 1 mm.

Examples 1 to 3

After the non-penetrated hollow protrusion 3 was formed, a hollow protruding implement 1 was manufactured following the procedures shown in FIGS. 7(*d*) and 7(*e*). Specifically, the distance from the tip of the hollow protrusion 3 was fixed at 300 µm, the laser output of the laser light 4L was fixed at 14 W, and the angle θ formed by the insertion direction ILe and the inclined direction ILf was fixed at 30 degrees. For hollow protruding implements of Examples 1 to 3, the irradiation time of the laser light 4L was changed to 0.015 ms, 0.02 ms, and 0.04 ms, respectively, and an opening 3*h* was formed by irradiating the hollow protrusion 3 with the laser light 4L.

Example 4

After the non-penetrated hollow protrusion 3 was formed, a hollow protruding implement 1 was manufactured following the procedures shown in FIGS. 7(*d*) and 7(*e*). Specifically, the distance from the tip of the hollow protrusion 3 was fixed at 300 μm, the irradiation time of the laser light 4L was fixed at 0.02 ms, and the angle θ formed by the insertion direction ILe and the inclined direction ILf was fixed at 30 degrees. For a hollow protruding implement of Example 4, the laser output of the laser light 4L was changed to 10 W, and an opening 3h was formed by irradiating the hollow protrusion 3 with the laser light 4L.

Examples 5 to 8

After the non-penetrated hollow protrusion 3 was formed, a hollow protruding implement 1 was manufactured following the procedures shown in FIGS. 7(d) and 7(e). Specifically, the laser output of the laser light 4L was fixed at 14 W, the irradiation time of the laser light 4L was fixed at 0.02 ms, and the angle θ formed by the insertion direction ILe and the inclined direction ILf was fixed at 30 degrees. For hollow protruding implements of Examples 5 to 8, the distance from the tip of the hollow protrusion 3 was changed to 200 μm, 500 μm, 700 μm, and 900 μm, respectively, and an opening 3h was formed by irradiating the hollow protrusion 3 with the laser light 4L.

Examples 9 and 10

After the non-penetrated hollow protrusion 3 was formed, a hollow protruding implement 1 was manufactured following the procedures shown in FIGS. 7(d) and 7(e). Specifically, the distance from the tip of the hollow protrusion 3 was fixed at 500 μm, the laser output of the laser light 4L was fixed at 14 W, and the irradiation time of the laser light 4L was fixed at 0.02 ms. For hollow protruding implements of Examples 9 and 10, the angle θ formed by the insertion direction ILe and the inclined direction ILf was changed to 15 degrees and 45 degrees, respectively, and an opening 3h was formed by irradiating the hollow protrusion 3 with the laser light 4L.

Performance Evaluation

The hollow protruding implements of Examples 1 to 10 were observed using a scanning electron microscope (SEM) to check whether or not burrs were formed around the opening on the outer surface of the hollow protrusion and also determine the inner diameter of the opening 3h on the inner surface 31 side and the inner diameter thereof on the outer surface side. Table 1 below shows the results.

piece the skin. Moreover, in the hollow protruding implements of Examples 1 to 10, the shape of the hollow protrusions and the shape of the openings were favorable. Thus, it can be expected that, according to the methods for manufacturing the hollow protruding implements of Examples 1 to 10, it is possible to continuously and efficiently manufacture hollow protruding implements that are precise in terms of the height of the fine hollow protrusions and the size of the openings.

INDUSTRIAL APPLICABILITY

According to the manufacturing method and the manufacturing apparatus of the present invention, fine hollow protrusions having openings can be formed with a precise shape, and burrs are unlikely to be formed around the openings on the outer surfaces of the hollow protrusions. Moreover, the fine hollow protruding implement of the present invention is capable of easily piercing the skin.

The invention claimed is:

1. A method for manufacturing a hollow protruding implement including a fine hollow protrusion having an opening, the method comprising:
a protrusion forming step of inserting a protrusion-forming projecting mold part into a base material sheet from one face side thereof, the base material sheet containing a thermoplastic resin, thereby forming a non-penetrated hollow protrusion projecting from another face side of the base material sheet;
a cooling step of cooling the non-penetrated hollow protrusion, the cooling step being performed after the protrusion forming step;
an opening forming step of forming an opening as a through hole in the non-penetrated hollow protrusion by using a contactless opening forming means disposed on the other face side of the base material sheet while the non-penetrated hollow protrusion is being cooled in the cooling step, and
in the opening forming step, the opening is formed in a state in which the projecting mold part is inserted in an interior of the non-penetrated hollow protrusion.

2. The method for manufacturing a hollow protruding implement according to claim 1,

TABLE 1

| Unit | Distance from tip of hollow protrusion 3 μm | Laser output W | Angle θ Degree | Irradiation time ms | Whether or not burrs were formed — | Inner diameter of opening on inner surface side μm | Inner diameter of opening on outer surface side μm |
|---|---|---|---|---|---|---|---|
| Ex. 1 | 300 | 14 | 30 | 0.015 | Not formed | 46 | 184 |
| Ex. 2 | 300 | 14 | 30 | 0.02 | Not formed | 47 | 208 |
| Ex. 3 | 300 | 14 | 30 | 0.04 | Not formed | 65 | 243 |
| Ex. 4 | 300 | 10 | 30 | 0.02 | Not formed | 30 | 160 |
| Ex. 5 | 200 | 14 | 30 | 0.02 | Not formed | 47 | 226 |
| Ex. 6 | 500 | 14 | 30 | 0.02 | Not formed | 55 | 182 |
| Ex. 7 | 700 | 14 | 30 | 0.02 | Not formed | 54 | 177 |
| Ex. 8 | 900 | 14 | 30 | 0.02 | Not formed | 70 | 169 |
| Ex. 9 | 500 | 14 | 15 | 0.02 | Not formed | 35 | 240 |
| Ex. 10 | 500 | 14 | 45 | 0.02 | Not formed | 64 | 205 |

As is clear from the results shown in Table 1, the hollow protruding implements of Examples 1 to 10 had no burrs on the outer surfaces and can be expected to be able to smoothly wherein, in the opening forming step, the opening is formed at a position offset from a center of a tip portion of the non-penetrated hollow protrusion.

3. The method for manufacturing a hollow protruding implement according to claim 1,
wherein a laser device is used as the contactless opening forming means.

4. The method for manufacturing a hollow protruding implement according to claim 3,
wherein, in the opening forming step, the opening is formed by irradiating laser light from the laser device onto the non-penetrated hollow protrusion from a direction that is inclined with respect to an insertion direction of the projecting mold part.

5. The method for manufacturing a hollow protruding implement according to claim 4,
wherein an angle that is formed by the insertion direction of the projecting mold part and the inclined direction in which the laser light is irradiated is from 5 to 85 degrees.

6. The method for manufacturing a hollow protruding implement according to claim 1,
wherein the projecting mold part has a heating means, and in the protrusion forming step, the base material sheet is heated and softened by the heating means.

7. The method for manufacturing a hollow protruding implement according to claim 6,
wherein a time for which the base material sheet is heated and softened by the heating means is from 0 to 10 seconds.

8. The method for manufacturing a hollow protruding implement according to claim 1,
wherein the projecting mold part has a heating means, and an ultrasonic vibration device is used as the heating means.

9. The method for manufacturing a hollow protruding implement according to claim 1,
wherein, in the protrusion forming step, an insertion speed at which the projecting mold part is inserted into the base material sheet is from 0.1 to 1,000 mm/sec.

10. The method for manufacturing a hollow protruding implement according to claim 1,
wherein, in the cooling step, the non-penetrated hollow protrusion is cooled in a state in which the projecting mold part is inserted in an interior of the non-penetrated hollow protrusion.

11. An apparatus for manufacturing a hollow protruding implement including a fine hollow protrusion having an opening, the apparatus comprising:
a protrusion forming section including a protrusion-forming projecting mold part that is disposed on one face side of a base material sheet containing a thermoplastic resin;
a cooling section that cools the non-penetrated hollow protrusion; and
an opening forming section including a contactless opening forming means that is disposed on another face side of the base material sheet,
wherein the apparatus is configured to insert the projecting mold part into the base material sheet from the one face side thereof, thereby forming a non-penetrated hollow protrusion projecting from the other face side of the base material sheet, and to subsequently form an opening as a through hole in the non-penetrated hollow protrusion by using the opening forming means from the other face side of the base material sheet while the non-penetrated hollow protrusion is being cooled by the cooling section, and
wherein the opening forming section is configured to form the opening in a state in which the projecting mold part is inserted in an interior of the non-penetrated hollow protrusion.

12. The apparatus for manufacturing a hollow protruding implement according to claim 11,
wherein the opening forming section is configured to form the opening at a position offset from a center of a tip portion of the non-penetrated hollow protrusion.

13. The apparatus for manufacturing a hollow protruding implement according to claim 11,
wherein the contactless opening forming means is a laser device.

14. The apparatus for manufacturing a hollow protruding implement according to claim 13,
wherein the opening forming section forms the opening by irradiating laser light from the laser device onto the non-penetrated hollow protrusion from a direction that is inclined with respect to an insertion direction of the projecting mold part.

15. The apparatus for manufacturing a hollow protruding implement according to claim 14,
wherein an angle that is formed by the insertion direction of the projecting mold part and the inclined direction in which the laser light is irradiated is from 5 to 85 degrees.

16. The apparatus for manufacturing a hollow protruding implement according to claim 11,
wherein the projecting mold part has an ultrasonic vibration that heats and softens the base material sheet.

17. A hollow protruding implement including a fine hollow protrusion having an opening,
wherein the opening is a through hole disposed at a position offset from a center of a tip portion of the hollow protrusion,
an inner diameter of the opening on an outer surface side of the hollow protrusion is greater than the inner diameter thereof on an inner surface side of the hollow protrusion, and
a space in the hollow protrusions is formed in a shape that conforms to the outer shape of the hollow protrusion.

18. The hollow protruding implement according to claim 17,
wherein the inner diameter of the opening gradually increases from the inner surface side of the hollow protrusion toward the outer surface side thereof.

19. The hollow protruding implement according to claim 17,
wherein the inner diameter of the opening on the inner surface side is from 1 to 500 μm.

20. The hollow protruding implement according to claim 17,
wherein the inner diameter of the opening on the outer surface side is from 1.1 to 15 times greater than the inner diameter thereof on the inner surface side.

21. The hollow protruding implement according to claim 17,
wherein an opening area of the opening on the outer surface side of the hollow protrusion is larger than the opening area of the opening on the inner surface side of the hollow protrusion.

22. The hollow protruding implement according to claim 17,
wherein the space in the hollow protrusion is formed in a conical shape that conforms to the outer shape of the hollow protrusion.

* * * * *